US006468219B1

(12) United States Patent
Njemanze

(10) Patent No.: US 6,468,219 B1
(45) Date of Patent: Oct. 22, 2002

(54) IMPLANTABLE TELEMETRIC TRANSCRANIAL DOPPLER DEVICE

(75) Inventor: Philip Chidi Njemanze, No 1 Uratta Road P.O. Box 302, Owerri (NG)

(73) Assignee: Philip Chidi Njemanze, Owerri (NG)

( * ) Notice: Subject to any disclaimer, the term of this patent is extended or adjusted under 35 U.S.C. 154(b) by 0 days.

(21) Appl. No.: 09/559,006

(22) Filed: Apr. 24, 2000

(51) Int. Cl.⁷ .................................................. A61B 5/00
(52) U.S. Cl. ............................ 600/454; 607/23; 607/24
(58) Field of Search ............................. 607/17–19, 23, 607/24; 600/459, 443, 437, 422, 455, 462, 465, 467, 480, 454, 486; 604/891, 500, 66

(56) References Cited

U.S. PATENT DOCUMENTS 5,188,106 A * 2/1993 Nappholz et al. .............. 607/24
5,484,404 A * 1/1996 Schulman et al. ............ 604/66

* cited by examiner

Primary Examiner—Marvin M. Lateef
Assistant Examiner—Ruby Jain

(57) ABSTRACT

The invention relates to a cerebral blood flow velocity monitoring system and method that comprises a transcranial Doppler ultrasound device that is adapted to be implanted in the human body, an oximeter, an external handheld computer and a drug delivery system. The system provides for monitoring of microembolic signals and operatively activates the drug delivery system for infusion of medication into the blood circulation for thrombolysis and neuroprotection.

20 Claims, 11 Drawing Sheets

IMPLANTABLE TELEMETRIC TRANSCRANIAL DOPPLER DEVICE

CROSS-REFERENCE TO RELATED APPLICATION

US PATENT DOCUMENTS

U.S. Pat. No. 5,188,106 Feb. 2, 1993 Nappholz et al. 607/24

U.S. Pat. No. 5,484,404 Jan. 1, 1996 Schulman et al. 604/66

BACKGROUND OF THE INVENTION

The present invention relates to cerebral blood flow velocity monitoring system and method specifically a transcranial Doppler ultrasound device adapted for implantation into the human body, for detecting microembolic signals and changes in cerebral blood flow velocity and operatively connected to a drug delivery system.

Human implantable physiological and/or chemical sensors and/or implantable fluid delivery systems of various forms are used in present day clinical practice. U.S. Pat. No. 5,484,404 is an example of such a system and is incorporated herein by reference.

U.S. Pat. No. 5,188,106 describes an apparatus and method that provides for monitoring of heart contractility and blood flow output from the heart to control an implantable cardiac assist or therapy device to maintain cardiac output without invading the left heart or the arterial system of the patient. The '106 patent is incorporated herein by reference.

While the '106 patent describes a system in which the physiologic parameter of interest for hemodynamic control is the cardiac output, that is, the amount of blood flow from the heart per unit time, the required indicia for brain blood supply is determined by peripheral reactions influencing the resistance and capacitance of cerebral blood vessels. The hemodynamic differences between the cardiovascular and cerebrovascular systems are further illustrated by the applicability of the "windkessel" model to the former as described in an article by Frank O. entitled "Die Grundform des arteriellen pulses," published in Z Biol, vol. 37, pp. 483–526 (1899), but not to the latter, as argued in an article by Njemanze P. C. et al., entitled "Fourier analysis of the cerebrovascular system," published in Stroke, vol. 22, pp. 721–726 (1991). Furthermore, there appears to be distinct regulatory mechanisms of blood flow in the cerebrovascular system as compared to the cardiovascular system. Cerebrovascular autoregulation has been characterized using transcranial Doppler technique in an article by Aaslid R. et al., entitled "Assessment of cerebral autoregulation dynamics from simultaneous arterial and venous transcranial Doppler recordings in humans," published in Stroke, vol. 22, pp. 1148–1154 (1991). The possibility that failure of cerebrovascular flow regulatory mechanisms such as in syncope may not be accompanied by fall in mean arterial blood pressure has been raised in an article by Njemanze P. C., entitled "Cerebral circulatory dysfunction and hemodynamic abnormalities in syncope during upright tilt test," published in Can J Cardiol, vol. 9, pp. 238–242 (1993). This work further emphasis the difference between cerebrovascular and cardiovascular systems thus requiring different monitoring approaches. Other publications by Njemanze P. C., entitled "Isoproterenol induced cerebral hypoperfusion in a heart transplant recipient," published in PACE vol. 16, pp. 491–495 (1992) and another article by same author entitled "Cerebrovascular dysautoregulation syndrome in a heart-lung transplant recipient," published in J Cardiovascular Tech, vol. 10, pp. 227–232 (1992), suggest that cardiopulmonary reflexes may not be implicated in this mechanism. Even more importantly the changes in cerebral circulation may precede changes in cardiovascular system as suggested in a report by Njemanze P. C. entitled "Cerebrovascular dysautoregulation syndrome complex—brain hypoperfusion precedes hypotension and cardiac asystole," published in Jpn Circ J, vol. 58, pp. 293–297 (1994). It therefore follows that the '106 patent may not be applicable to the cerebrovascular system. What is therefore desirable is a device that is responsive to blood flow changes detected in the cerebrovascular system in conditions such as stroke.

The annual incidence of stroke is approximately 700,000 per annum in the United States according to the statistics provided in a work by Broderick J., et al., entitled "The Greater Cincinnati/Northern Kentucky Stroke Study: preliminary first-ever and total incidence rates of stroke among blacks," published in Stroke, vol. 29, pp. 415–421 (1998). Ischemic strokes account for 80% of all stroke types. The high incidence and associated burden of disease of stroke have led to an interest to develop accurate predictors and prevention strategies. It is therefore desirable to have non-invasive techniques to identify surrogate markers of stroke events and their associated outcome. One such approach has been to utilize non-invasive cerebral blood flow velocity monitoring using transcranial Doppler ultrasound to measure microembolic signals also called high-intensity transient signals known to precede stroke events. Microembolic signals have been observed in patients with implanted mechanical and prosthetic devices and there are also spontaneously occurring microembolic signals in a variety of clinical conditions. Microembolic signals are identified by criteria set forth by the Consensus Committee of the Ninth International Cerebral Hemodynamic Symposium in a publication entitled "Basic identification criteria of Doppler microembolic signals," published in Stroke, vol. 26, pp. 1123 (1995).

The occurrence of microembolic signals has been recorded during open-heart surgery, carotid endarterectomy and in patients with prosthetic heart valves, ventricular assist devices and those with atrial fibrillation. The association of microembolic signals with neurological and neuropsychological deficits in patients after open-heart surgery has been described in an article by Clark R. E., et al., entitled "Microemboli during coronary artery bypass grafting genesis and effects on outcome," published in J Thorac Cardiovasc Surg, vol. 109, pp. 249–258 (1995).

Spencer M. in an article entitled "Transcranial Doppler monitoring and causes of stroke from carotid endarterectomy," published in Stroke, vol. 28, pp. 685–691 (1997), ascribed postoperative cerebral ischemia in patients with carotid endarterectomy to the high rates of microembolic signals during surgery and in the immediate postoperative period. The enormity and severity of the problem of symptomatic and asymptomatic microemboli remains to be fully elucidated.

One object of the present invention is to use it in conjunction with ventricular assist devices. Considering that while tens of thousands of United States patients need a donor heart each year, only about 2,000 receive one. The ventricular assist devices have been shown to add months, even years, to patients' lives while the wait for donor heart to become available. Close to three thousand patients have received ventricular assist devices in Europe and America. One major limitation of the ventricular assist devices is the occurrences of clinical thromboembolism in up to 30%, dependent on device type and implantation center. Wagner W. R., and Johnson P. C., in an article entitled "Therapeutic techniques for reducing thrombosis after cardiovascular implants, published in a book by Klizman B., (ed.) entitled "Problems in General Surgery", published by JB Lippincott Co., Philadelphia, Pa.: chapter 11, pp. 241–246 (1994), have suggested that thromboembolism remains a significant impediment to the choice application of ventricular assist devices. However, they demonstrated prolonged life of the patients with cardiomyopathy using ventricular assist devices until heart transplantation, which makes identification and prevention of thromboembolism an important strategy in patient care for prevention of strokes in this population. Wilhelm C. R., et al., in an article entitled "Measurement of hemostatic indexes in conjunction with transcranial Doppler sonography in patients with ventricular assist devices," published in Stroke vol. 30, pp. 2554–2561 (1999), have demonstrated that microembolic signals identified using transcranial Doppler are related to increased hemostatic activity in patients with ventricular assist devices. Ventricular assist devices of different designs are now in clinical use. Left ventricular assist device (Novacor Left Ventricular Assist System—Baxter Healthcare, Deerfield, Ill.) and bi-ventricular assist device (Thoratec® VAD system) are offered commercially for implantation in patients. Measures to reduce thrombus formation include the use of Thoralon®, (Thoratec®) a patented thromboresistant and biocompatible material with thromboresistant properties. However, significant microembolic signals still persist. An evaluation of the thromboembolic events was carried out in a recent article by Wilhelm C. R., et al., entitled "Measurement of hemostatic indexes in conjunction with transcranial Doppler Sonography in patients with ventricular assist devices," published in Stroke vol. 30, pp. 2554–2561 (1999). The authors classified thromboembolic events as transient ischemic attacks (symptoms resolving within 24 hours) or cerebrovascular accidents (permanent deficit or symptom duration >24 hours). Thirteen thromboembolic events, including five cerebrovascular accidents and eight transient ischemic attacks, were recorded in 12 (44%) of the 27 patients (of which 21 were males and 6 were females). For all patients, microembolic signals were not observed in any transcranial Doppler measurements prior to implantation. Temporally, seven of the events occurred within the first four weeks after implantation. Of the twelve patients with Novacor left ventricular assist devices, one half had microembolic signals detected compared with 100% of the patients with Thoratec® ventricular assist devices (p=0.0001 vs Novacor) and 100% of patients with Thoratec® BiVADs (p=0.014 vs Novacor). The generation of thrombin in vivo was related in a highly significant manner to the presence of microembolic signals showering in patients with ventricular assist devices. All patients were on anticoagulation regimen. The results of this study showed that it would be desirable to have a system that may diagnose and prevent thromboembolus in patients with ventricular assist devices. The present invention accomplishes a continual detection of microembolic signals and provides countermeasures to prevent neurological deficits.

Another clinically related use of the present invention is in patients with atrial fibrillation. Atrial fibrillation causes stasis of blood flow in the left atrial appendage, leading to thrombus formation and embolic stroke. Although, atrial fibrillation is associated with a six-fold increased risk of stroke, most patients with atrial fibrillation never suffer stroke, however, those with increased microembolic signals are most likely to suffer strokes. It is therefore desirable to continually detect microembolic signals and initiate countermeasures to prevent thromboembolus.

Another clinical use of the present invention relates to patients with carotid artery stenosis. It has been reported that the frequency of microembolic signals in patients with atrial fibrillation appears to be lower than that found in carotid artery stenosis as has been reported by Cullinane M., et al., in an article entitled "Asymptomatic embolization in subjects with atrial fibrillation not taking anticoagulants: a prospective study," published in Stroke, vol. 29, pp. 1810–1815 (1998). Similarly, patients with aortic arch atheroma are also expected to have increased microembolic signals and may benefit from use of the present invention.

A further object of the present invention is its use in patients with prosthetic heart valves. Prosthetic heart valves may be associated with formation of thrombus and thromboembolism. Thrombus and thromboembolism are known complications of mechanical heart valves and can result in serious neurological deficits or death. Certain measures in the design of new prosthetic valves have been undertaken to reduce the danger of thromboembolus. Georgiadis D., et al., in an article titled "Transcranial Doppler detection of microemboli in prosthetic heart valve patients: dependency upon valve type," published in Eur J Cardiothoracic Surg, vol. 10, pp. 253–258 (1996), described asymptomatic microembolic signals in patients with prosthetic heart valves. To prevent these complications a common treatment involves life-long anticoagulant therapy. However, continuous anticoagulant therapy itself leads to increased risk of anticoagulant-related hemorrhage. It is therefore desirable to have timely detection of the microembolic signals and target the use of the anticoagulant therapy only when the microembolic signals occur. This approach is accomplished with the present invention.

Similarly, prosthetic vascular grafts and stent devices are becoming more common for clinical applications. Various rigid stent devices have been utilized to hold and support bioprosthetic implants, such as heart valves. Similarly, intracranial stent devices have been described. Theron J. G., et al., in an article entitled "Carotid artery stenosis: treatment with protected balloon angioplasty and stent placement," published in Radiology, vol. 201, pp. 627–636 (1996), described the carotid angioplasty and stent placement as an alternative to carotid endarterectomy for treatment of carotid stenosis. Common to all these devices are thromboembolic complications known to result from turbulent blood flow through vascular grafts. This has been associated with abrupt variations in the diameter of the blood vessel lumen, as may result from improper size matching of the vascular implant graft. The early detection and remedy of severe thromboembolic complications as a result of vascular implant grafts and stents are objects of the present invention.

Yet another object of the present invention is to prevent stroke in high-risk group of patients. For example, a patient who has suffered a transient ischemic attack is thirteen times at greater risk of suffering a stroke. This risk further increases if the patient is elderly, hypertensive, with >70% carotid stenosis, diabetic, smokes and has coronary heart disease. Prevention of stroke in this group of patients is feasible using the device described in this disclosure.

Patients with stroke may benefit from early thrombolytic therapy within 3 hours of onset of symptoms as described in the protocol by the National Institute of Neurological Disorders and Stroke rt-PA Stroke Study Group, entitled "Tissue plasminogen activator for acute ischemic stroke," published in N Engl J Med, vol. 333, pp. 1581–1587 (1995). However, crucial time is lost between clinical detection of the thromboembolic event and administration of this life-saving thrombolytic therapy. By use of the present invention implanted in a patient at risk of stroke, detection of thromboembolus is within seconds and initiation of thrombolytic therapy could be immediate, so that, time is gained and life saved. Moreover, it has been hypothesized in an article by Alexandrov A. V., et al., entitled "High rate of complete recanalization and dramatic clinical recovery during tPA infusion when continuously monitored with 2-MHz time in the future preclude the use of implanted electrodes for EEG recordings and subsequent epilepsy surgery on the temporal lobe in this category of patients. Preliminary findings by Njemanze P. C., et al., disclosed in an article entitled "Cerebral blood flow velocity and EEG amplitude in generalized seizures: a case study," published in J Neuroimag, vol. 2, pp. 151–155 (1992) have shown that marked cerebral blood flow velocity increases associated with onset of seizure activity could be detected within seconds before onset of clinical manifestation. The present invention provides means that would allow for injection of anti-epileptic medication to remedy the seizures before clinical onset and is particularly of essence in patients prone to have 'status epilepticus'. Drugs like diazepam and newer fast-acting anti-epileptic drugs could be injected via internal or external drug delivery systems telemetrically responsive to the implanted transcranial Doppler ultrasound device in seizure patients.

Similarly, the present invention could be applied to patients requiring defibrillation. In an article by Njemanze P. C., entitled "Cerebrovascular dysautoregulation syndrome complex—brain hypoperfusion precedes hypotension and cardiac asystole," published in Jpn Circ J, vol. 58, pp. 293–297 (1994), the drop in cerebral blood flow velocity was shown to precede cardiac asystole by as much as two minutes. It is therefore desirable to gain time by telemetrically synchronizing the function of the implanted transcranial Doppler ultrasound device and the defibrillator. Commercially available implanted defibrillators from several vendors such as Medtronic Inc. Minneapolis, Minn. or external defibrillators for example Model HP S01/E01/EM01 Heartstream ForeRunner AED by Healthcare, Agilent (Hewlett Packard subsidiary located at Andover Mass.) could be adapted for this application in patients prone to severe arrhythmia.

Another object of the present invention is monitoring of patients with obstructive sleep apnea. Diomedi M., et al., in an article entitled "Cerebral hemodynamic changes in sleep apnea syndrome and continuous positive airway pressure treatment," published in Neurology, vol. 51, pp. 1051–1056 (1998), have suggested that snoring and sleep apnea are associated with increased risk of stroke and attributed this to diminished cerebral vasodilator reserve. The latter was studied using transcranial Doppler technique. Presently, available techniques for delivering airway flow use the patient's snoring to adjust the pressure settings. However, changes in cerebral blood flow velocity precede these other variables. It is therefore desirable to have long-term monitoring of cerebral blood flow velocity in conjunction with oximetry as a means for regulating nasal continuous positive airway pressure in patients with sleep apnea. The system of the present invention could be programmed to sound an audible alarm to patients with sleep apnea at the appropriate time. Several oximetry devices are available from a number of vendors such as Mallinckrodt at Tucson, Ariz. The present invention using cerebral blood flow velocity in conjunction with indicia of oximetry could telemetrically regulate the nasal continuous positive airway pressure delivered from a device such as Solo® Plus LX CPAP system obtainable from Respironics®, a company in Pittsburgh, Pa.

A further object of the present invention is to use the measured cerebral blood flow velocity to perform a workload assessment. The matching of cerebral blood flow velocity levels to increased psycho-physiologic workload in the rehabilitation phase after stroke could be performed in a more structured manner using the present invention.

SUMMARY OF THE INVENTION

The present invention overcomes some or all of the shortcomings of the prior art by early detection of microembolic signals and cerebral blood flow velocity monitoring using a transcranial Doppler ultrasound device adapted for implantation into the human body and an external handheld computer.

Additionally, there is provided an automatic triggering of the computer-programmed function of an infusion pump to inject a thrombolytic agent (for example tissue plasminogen activator (rt-PA), heparin, etc) into the vein (or artery) of the patient. Combined intravenous and intra-arterial rt-PA has been studied by Lewandowski C. A., et al., disclosed in an article entitled "Combined intravenous and intra-arterial rt-PA versus intra-arterial therapy of acute ischemic stroke: emergency management of stroke (EMS) bridging trial," published in Stroke, vol. 30, pp. 2598–2605 (1999). Information about a thrombolytic agent rt-PA is provided in the "Physicians" desk reference," 53 edition, Medical Economics Company, Montvale, N.J.: pp. 1057–1061 (1999), under a trade-name Activase® (generic name Altepase recombinant) produced by recombinant DNA technology by Genentech Inc., a company in San Francisco, Calif.

The special embodiment of this invention is illustrated in the specification, it includes block and schematic diagrams for the format of the instrumentation, and how the system functions is shown by way of example. The human involved will be referred to as "patient" by way of example. The system comprises a transcranial Doppler ultrasound device adapted for implantation in the human body, oximeter, external handheld computer, and an implantable mini-drug delivery system or external drug infusion system. The present invention may use conventional transcranial Doppler pulsed wave 2 MHz ultrasound transducer, however, the continuous wave mode could in principle be applied. Multigate Doppler sampling covering a range of depths will provide even better access to cerebral vessels and is a preferred option. These and other modifications will appear obvious to anybody skilled in the art. The implantable transcranial Doppler ultrasound device comprises a transducer placed on the acoustic window of the temporal bone above the zygomatic arc and focused on the middle cerebral arteries unilaterally (or bilaterally) by way of example, a voltage generator and gate, a receiver and gate, microprocessor that executes the programs such as spectral analysis and sending the information to the external handheld computer via a radio-frequency (RF) transmitter/receiver. The unit detects the respiratory status using measurement of oxygen saturation of hemoglobin. The entire unit is powered using long battery life such as lithium battery similar to that used for implanted pacemakers. Low modulus Ti—Nb—Zr alloys could be used for fabrication material for the implanted parts to provide enhanced biocompatibility and hemocompatibility. Furthermore, at least one surface of the implantable device could be covered with rt-PA to avoid inflammatory reactions of the body and formation of fibrous capsules, which ordinarily occur after implantation.

The external base unit comprises a handheld computer with an attached RF transmitter/receiver and antenna, a central processing unit (included in a microcomputer), a loudspeaker, a monitor for spectral display, a keyboard, a global positioning system and communication access to the Internet. Several modifications of the handheld computer could be used for the purpose of this invention including integration of the features in a cellular telephone or use of a handheld computer device such as Visor™ Platinum from Handspring Inc. Mountainview, Calif. Other features such as voice-activated controls, global positioning (GPS) module, full Internet access and high speed modem already available in commercial handheld computers and could well be incorporated into the present invention for easy use.

The internally implanted drug delivery pump could be physically connected to the implanted transcranial Doppler ultrasound device or made telemetrically responsive. The drug delivery system could comprise several compartments of the drug reservoir, with the pump responsive to signals from the transcranial Doppler ultrasound device to regulate release of the needed medication via a catheter grafted into the vein (or artery), to infuse the medication in a similar manner as disclosed in U.S. Pat. No. 5,484,404 by Schulman et al. The several compartments of the drug reservoir could be used to store medication that is externally introduced by percutaneous injection under X-ray control. Rt-PA for example, could be synthesized using the complementary DNA (cDNA) for natural human tissue-type plasminogen activator obtained from a melanoma cell line. Improvements in genetic and technical procedures of the present manufacturing process could make it possible to produce the rt-PA within micro-compartments, and creating an internal drug reservoir that would preclude external refill of the medication.

The external drug delivery system comprises a programmable pump, a radio frequency receiver, intravenous cannula and syringe/reservoir containing the thrombolytic agent. There is provided a communication means between the implanted transcranial Doppler ultrasound device and the external drug delivery system.

In order to use the system, the patient could enter relevant information such as subjective symptoms into the handheld computer and send the information to the attending physician via the Internet. The attending physician using his/her physician's transcranial Doppler monitoring," published in Stroke, vol. 31, pp. 610–614 (2000), that continuous ultrasonic energy transmission focused on clot location by transcranial Doppler monitoring may expose clot surface to action of tPA. This supports earlier report by Lauer C. G., et al., entitled "Effect of ultrasound on tissue-type plasminogen activator thrombolysis," published in Circulation, vol. 86, 1257–1264 (1992).

Yet another application of the present invention can be seen when one reviews the current use of neuroprotective agents in clinical trials. The use of the neuroprotective agents of the class N-methyl-D-aspartate (NMDA) antagonists was based on the finding that an ischemic brain injury produces elevated levels of the excitatory neurotransmitter glutamate, which leads to excessive stimulation of the NMDA receptor as described in an article by Lees K. R., entitled "Cerestat and other NMDA antagonists in ischemic stroke," published in Neurology, vol. 49, pp. S66–S69 (1997). The use of potentially effective neuroprotective agents such as NMDA antagonists has particular appeal in acute stroke, because these compounds are not associated with an increased risk of hemorrhage and could therefore be administered without a screening brain imaging (CT scan or MRI). The precise time window to administer neuroprotective agents is not known. Animal studies demonstrate effectiveness when NMDA antagonists are administered minutes after an infarction as demonstrated in a work by Simon R, and Shiraishi K., entitled "N-methyl-D-aspartate antagonist reduces stroke size and regional glucose metabolism," published in the Annals of Neurology, vol. 27, pp. 606–611 (1990). It is therefore desirable to have a means to detect an acute stroke event seconds to minutes after onset and trigger the administration of a neuroprotective agent. This precise goal can be accomplished with use of the present invention.

Yet another object of the present invention is the use of combined acute therapies in stroke. Recent experimental evidence obtained in the work by Heiss W. D., et al., entitled "Which targets are relevant for therapy of acute stroke?," published in Stroke, vol. 30, pp. 1468–1489 (1999), suggests a beneficial effect of the use of the neuroprotective agents concomitantly with reperfusion therapy. Grotta J. C. in an article entitled "Acute stroke therapy at the millennium: consummating the marriage between the laboratory and bedside: the Feinberg Lecture," published in Stroke, vol. 30, pp. 1722–1728 (1999), suggested combinations of thrombolytic and neuroprotective therapies. One of the benefits is that neuroprotective drugs may extend the therapeutic window for thrombolysis. Secondly, thrombolysis which promotes acute reperfusion, is likely to facilitate higher concentrations of neuroprotective agent in the critically under perfused penumbral region. It is therefore desirable to have a non-invasive technique that will detect acute stroke events and trigger the administration of neuroprotective as well as thrombolytic agents. The clinical trial in acute stroke using neuroprotective agent Selfotel (Avantis) yielded disappointing results when administration was delayed usually within three to six hours after stroke, as described in the protocol of a report by Davis S. M., et al., entitled "Selfotel in acute ischemic stroke. Possible neurotoxic effects of an NMDA antagonist," published in Stroke, vol. 30, pp. 347–345 (2000). The authors ascribe some of the blame to the poor choice of time windows for neuroprotective strategies. This problem is overcome by use of the present invention.

Yet another object of the present invention is the synchronization of function of the transcranial Doppler ultrasound device with other implanted mechanical devices and external physiologic assist devices. The function of a pacemaker could be synchronized with that of the implanted transcranial Doppler ultrasound device, for example, cerebral blood flow velocity reduction during pacing could automatically trigger a functional mode of a pacemaker to maintain cerebral perfusion in a feedback loop, thereby preventing pacemaker syndrome. Njemanze P. C., in an article entitled "Cerebral circulatory changes in a case of pacemaker syndrome," published in J Cardiovasc Technol, vol. 11, pp. 105–109 (1993), described a case where the function of the pacemaker was associated with reduction of cerebral blood flow velocity. Predisposition to syncope could be assessed using threshold values established for syncope as described in an article by Njemanze P. C., entitled "Critical limits of pressure flow relation in the human brain," published in Stroke, vol. 23, pp. 1743–1747 (1992). The function of the pacemaker could be regulated by telemetric communication between the present invention and the implanted pacemaker.

A further advantage of this invention is that it will allow for event-related monitoring of the cerebral blood flow velocity in seizure disorders. During seizures there could be a brief period of cessation of blood flow to the brain. This was disclosed in an article by Njemanze P. C., et al., entitled "Cerebral blood flow velocity and EEG amplitude in generalized seizures: a case study," published in J Neuroimag, vol. 2, pp. 151–155 (1992). This may influence mortality and morbidity in intractable seizure disorders. It is therefore desirable to have a system that documents the state of cerebral blood flow velocity measurements during seizure activity. This could be synchronized with simultaneously recording of video electroencephalography. The present invention allows for detection and long-term monitoring of seizure events especially in cases of intractable seizures. This approach will provide therapeutic measures and may at some identification number and access password could carry out review of the technical parameters of the implanted transcranial Doppler ultrasound device including serial number of the device, lot number, power source status and self-test diagnostic programs via the Internet. The attending physician could alter the program of the pump such a bolus dose, functional regulation of the transcranial Doppler signals including depth, artifact exclusion criteria, and even review current files of microembolic signal rate before and after each drug delivery regimen. The authorization for the physician to alter the functionality of the system is subject to drug prescription guidelines. Restricted Internet access via specified websites ensure strict compliance with the ethical codes implicated in the patient care services.

Another feature of the present invention provides a communication means to alert the emergency medical service team by automatically dialing the service via phone line or wireless connection in the event of a stroke. The handheld computer reads the coordinates of the location of the patient within a town from an incorporated global positioning system device. Such global positioning system devices are available from a number of vendors such as Magnavox, a company in Torrance, Calif. The system provides means for the patient to override any false-positive calls at initiation.

The transcranial Doppler ultrasound device could be adapted for implantation on one side of the body to monitor unilateral carotid artery system considering that stroke will occur at a higher frequency on the side with greater carotid plaque lesion. The asymmetric occurrence of carotid plaque lesions in the carotid systems has been related to handedness as described in an article by Njemanze P. C., entitled "Handedness and carotid plaque lesion" published in Stroke, vol. 23, pp. 1679–1680 (1992) and a related article by same author entitled "Carotid stenosis determines impairment of ipsilateral dexterity in stroke," published in Stroke, vol. 31, pp. 545–546 (2000). It is therefore of essence to perform noninvasive carotid color flow Doppler imaging studies to determine plaque lesion size, plaque morphology including ulcerations, and likely plaque composition. The choice of the side for the implant would be based on the side with greater clinical and B-mode ultrasound risk for microembolic signals and the rate of detection of microembolic signals by conventional transcranial Doppler monitoring of the ipsilateral carotid system. However, bilateral implantations focusing on two vessels (for example, left and right middle cerebral arteries or internal carotid arteries) are feasible using bilateral transcranial Doppler ultrasound device with two ultrasound probes. It may be possible to have left and/or right detection trigger pump release of the thrombolytic agent. Bilateral implantations may be necessitated if there are separate risk factors in two vascular territories for example in the anterior versus posterior cerebral circulation.

These and other objects of the invention may become more apparent to those skilled in the art upon reviewing the description of the invention as set forth hereinafter, in view of its drawings.

DESCRIPTION OF THE PREFERRED EMBODIMENT

Figure 1:
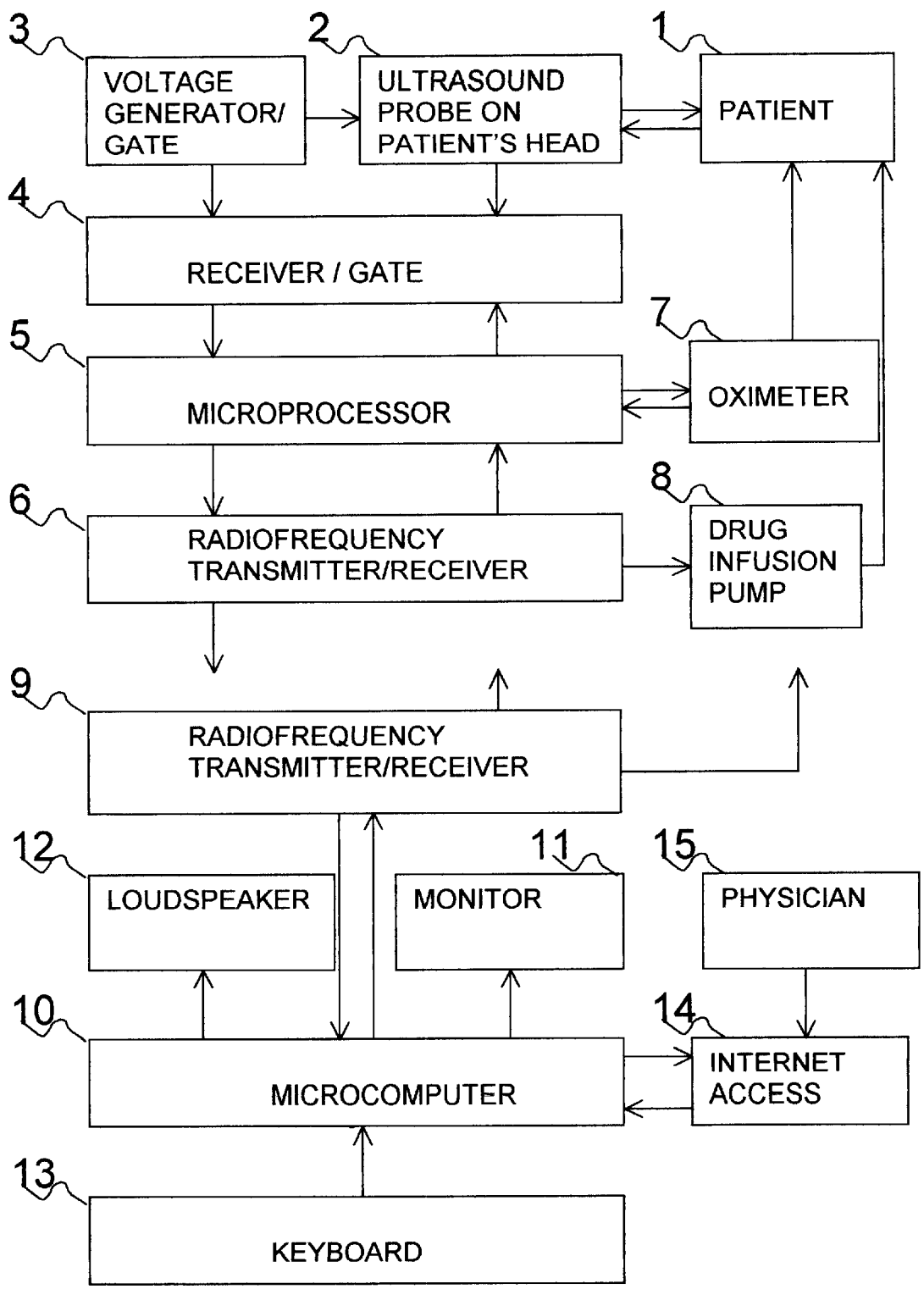
FIG. 1 shows the schematic diagram of the present invention.

FIG. 1 shows the schematic diagram of one embodiment of the present invention attached to a patient 1, with the ultrasound probe housing 2 placed on the temporal bone on the head; transcranial Doppler ultrasound device including a voltage generator/gate 3 a receiver/gate 4 that allow a selection of depth at which velocity of moving red blood cells can be measured and to detect motion of microembolic signals. The microprocessor 5 processes the spectral data in the usual manner as described for pulsed and continuous wave Doppler in the book by Kremkau F. W., "Diagnostic ultrasound: principles, instruments, and exercises," Third edition, published by W. B. Saunders Co., Philadelphia: (1989). However, the spectral waveform and audio signals are transmitted via a radio frequency transmitter/receiver 6 to another transmitter/receiver 9 attached to an external handheld computer 10, which displays the spectral data on the monitor 11 and plays the audio signals on the loudspeaker 12. The patient or medical personnel can view the spectral information and listen to the audio signals. It is possible for the patient to make authorized inputs into the program of the system using the keyboard 13, for example, to input the clinical symptoms related to a particular event. The system can be programmed to automatically access the Internet 14 and use the "File Transfer Procedure" (FTP) to move files containing information that may include spectral data, microembolic signal rate, patient personal data, equipment serial number and lot number to the attending physician or emergency medical service personnel. Conversely, the attending physician 15 can alter the program of the system including pump bolus dose discharge rate, insonation depth, new artifact exclusion criteria, and even review records on microembolic signal rate before and after each drug delivery regimen. In addition, a built-in oximeter 7 that detects oxygen saturation in blood is used to assess the respiratory status. The system on detection of microembolic signals could generate a trigger signal to activate an internally implanted infusion pump or an external infusion pump 8. In a preferred system, the infusion is implanted and receives control signals via a direct or telemetric connection. For example, when the infusion pump is built-in with the transcranial Doppler ultrasound device and placed in the subcutaneous space below the clavicle, an attached catheter could be placed at a selected in-vivo site such as the subclavian or cephalic vein.

Figure 2:
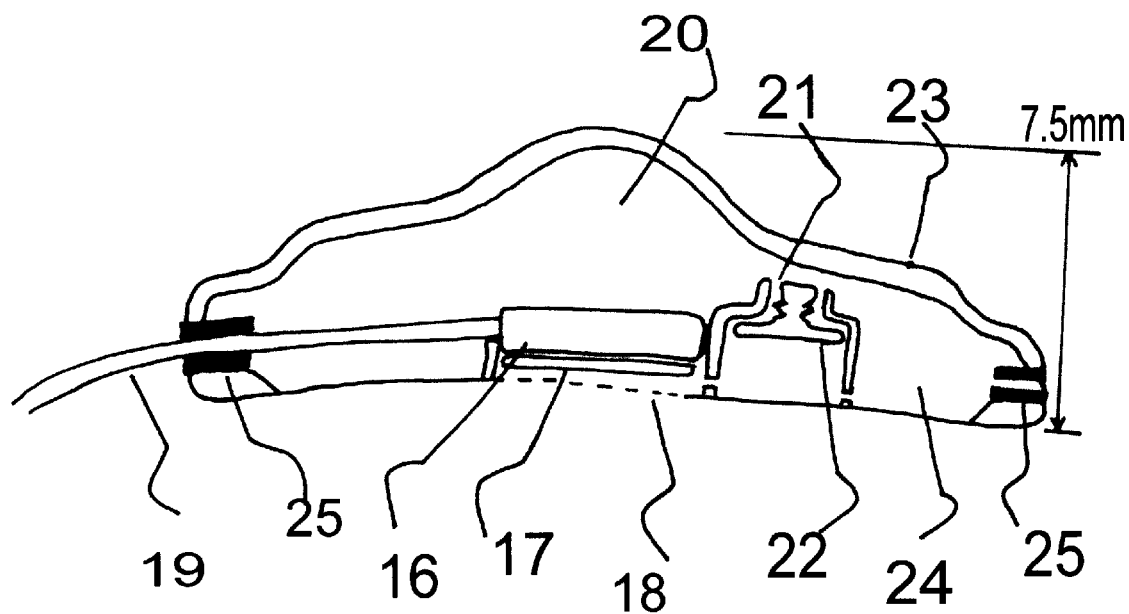
FIG. 2 shows the flexible silicone elastomer housing and an embedded piezoelectric ceramic transducer within a contoured polypropylene base.

FIG. 2 shows the flexible silicone elastomer probe housing, containing an embedded ultrasound transducer 16 placed on a contoured polypropylene base. Similar silicon elastomer housing have been used for cerebrospinal fluid flow control valves and could be obtained from Pudenz-Schulte Medical, a company in Santa Barbara, Calif. A solid ultrasonic biomedical couplant hydrogel sheet 17, and a thin film of hydrophilic polymer 18 provide means for transfer of ultrasound energy between the ultrasound transducer and the patient's head. A reservoir 20 temporarily stores the humectant such as triethylene glycol or glycerin, which drains through an upper inlet 21 into the silicon membrane valve 22. After drainage of the gel through the membrane valve 22, the reservoir 20 fills with air and provides an air cushion in the probe housing, which is required for attenuation of the ultrasound beam propagation in the reverse direction. The gel is refilled via a radiopaque dot marked needle injection site 23 into a reservoir 24. The reservoir is made of deformable silicon elastomer with pores at the base to allow a portion of the gel to flow to the surface of the probe. Both ends of the probe housing have radiopaque marks 25. The size of the probe housing vary and as shown could be of height 7.5 mm and diameter of 32 mm by way of example. The height of the probe housing is chosen such that it does not protrude sideways to alter the side profile of the patient's head and is well within the area covered by the hairline. In effect there is no cosmetic defect produced by the implantation of the probe housing.

The transducer 16 is firmly attached to the proximal end of the transducer cable 19, while the distal end is connected to the transcranial Doppler ultrasound device by means of detachable connector. The said cable could be additionally covered with silicon elastomer tubing impregnated with white barium sulfate to provide radiopacity for its entire length. The latter radiopaque cover provides means to monitor appearance of wire cable kink that may disturb the functionality of the transducer. However, the sillicon eclastomer cable cover is made of kink resistant material.

Figure 3:
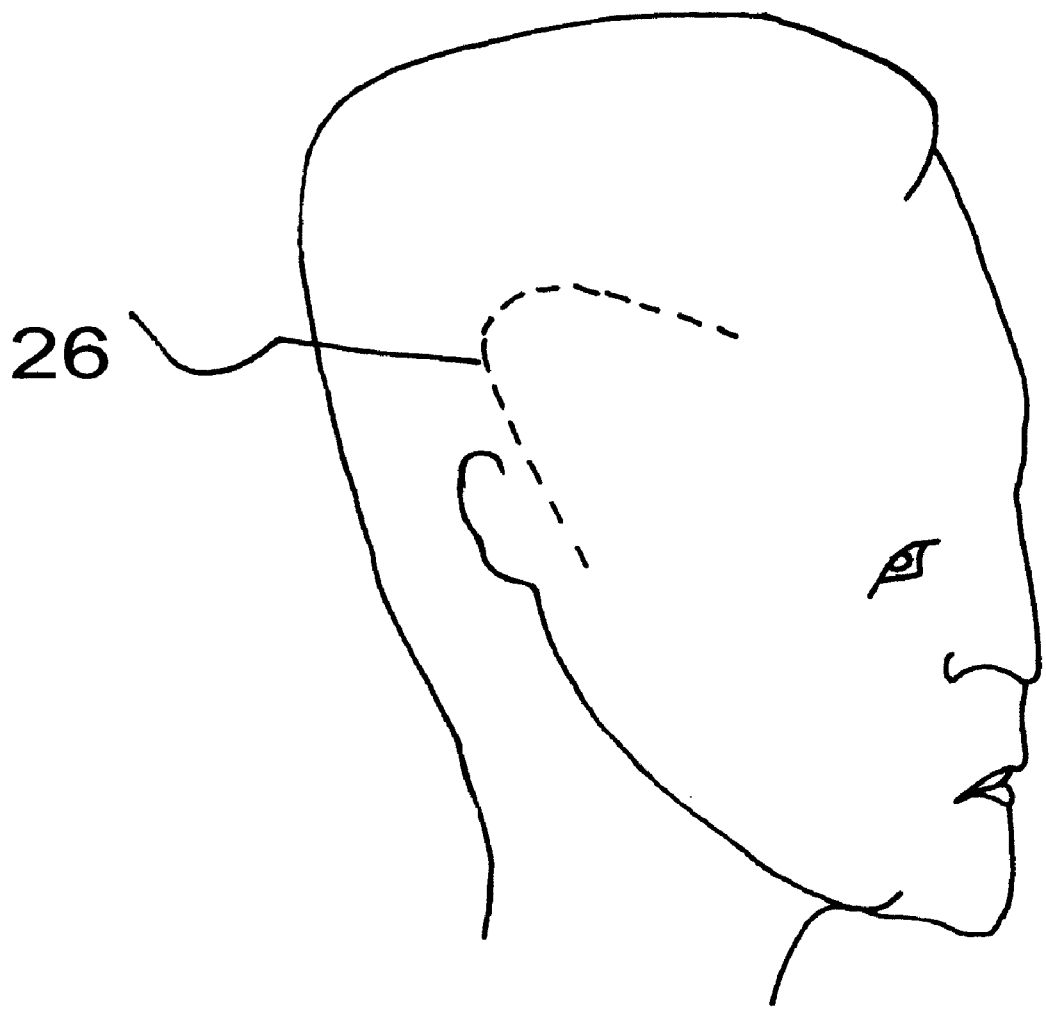
FIG. 3 shows the line of incision for implantation of the transcranial Doppler probe housing.

FIG. 3 shows the line of incision 26 for implantation of the transcranial Doppler probe housing. After the usual patient preparation for surgery, anesthesia, and aseptic procedures for surgical field preparation on a shaved skin, the line of incision 26 is made as shown by way of example. Several variations of the incision line are possible provided the superficial temporal artery is not severed.

Figure 4:
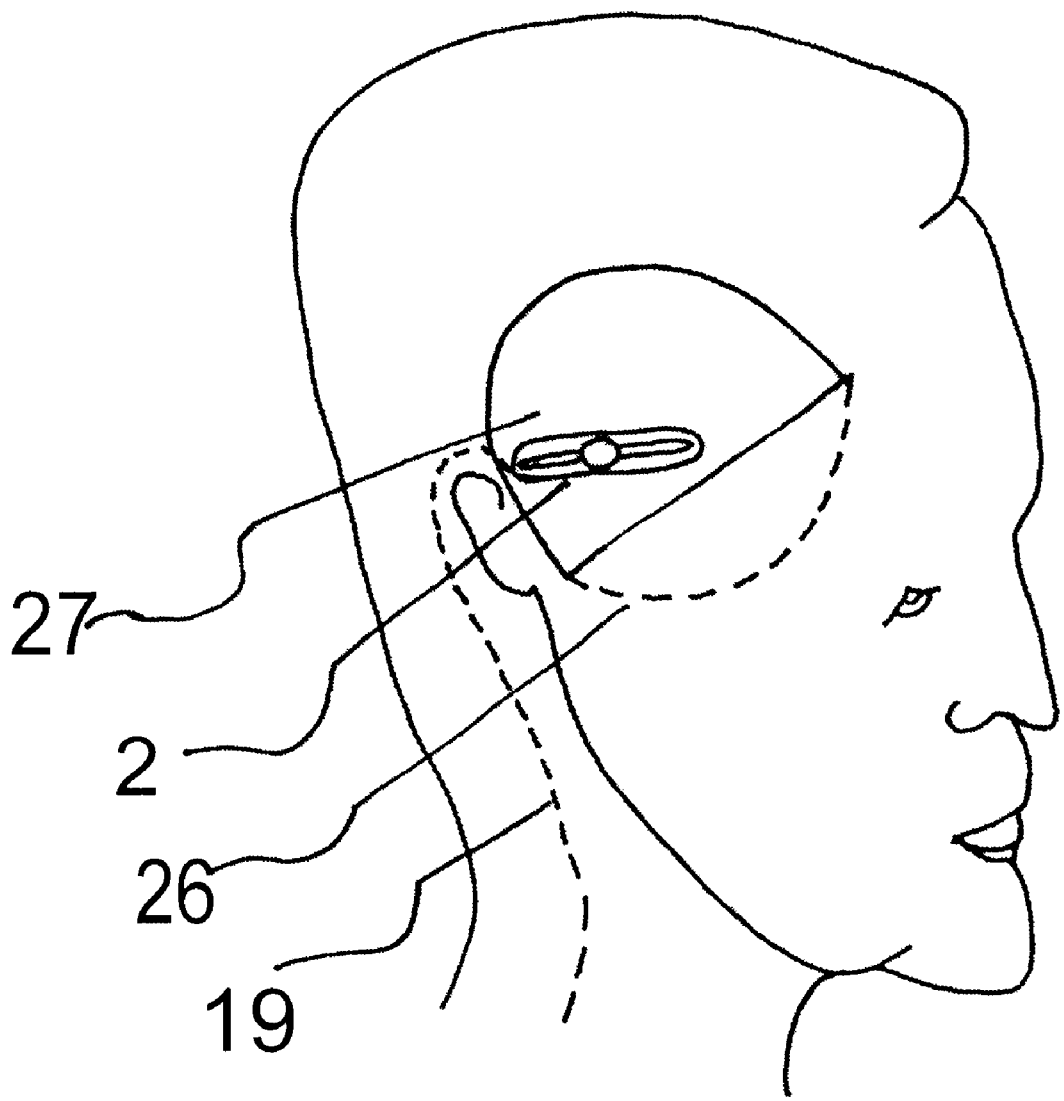
FIG. 4 shows the placement of the probe housing directly on the temporal bone above the zygomatic arch and the tunneling route of the transducer cable.

FIG. 4 shows exposure of the temporal bone 27 by removing the overlying skin. The probe housing, transducer cable and transcranial Doppler ultrasound device are packaged in a sterile pack. The probe housing 2 is aseptically removed from the pack and placed on the temporal bone above the zygomatic arc. The transcranial Doppler ultrasound device is aseptically implanted in the subcutaneous pocket below the clavicle. The external handheld computer 10, is placed at a distance from the sterile area but in eye view of the operator-surgeon. The system is then activated and the surgeon with the help of an assistant optimizes the Doppler waveform signals. Once the best possible spectral signals are obtained on the monitor 11 of the external handheld computer 10 the operational parameters are saved and the site of the probe housing on the temporal bone is marked. The surface area of the bone in the marked region is prepared with an abrasive operating instrument to create a rough bone surface on the marked bone region. The surface preparation instrument in some cases could be an adapted bone drill used to thin the bone if there is a poor acoustic window or when no window exists at all and the patient requires an implant. The firm polypropylene base of the probe housing 2 can be affixed to the temporal bone by means of a pre-applied adhesive surface at the polypropylene base and/or by means of application of adhesive semi-liquid glue. The said glue could be removed when required by using a variety of substances including a conventional nail polish remover by way of example.

Figure 5:
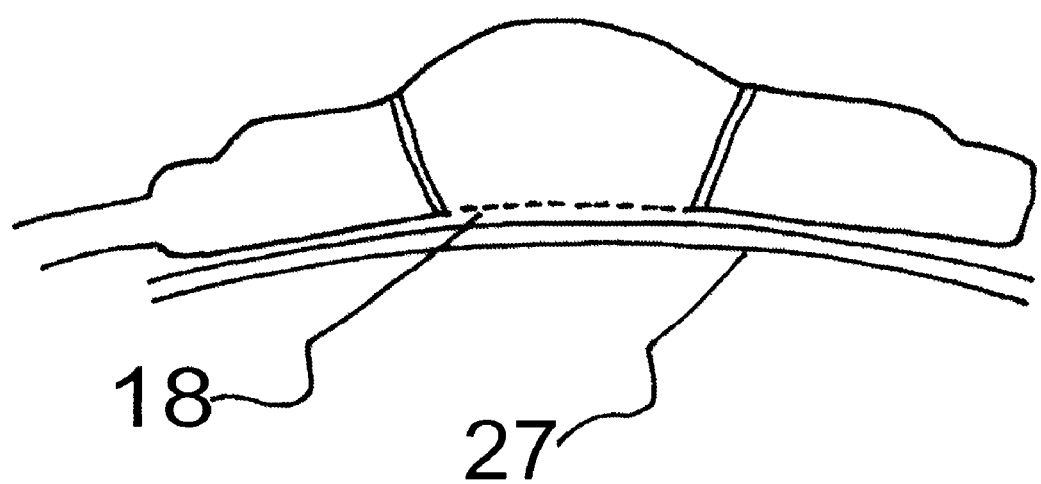
FIG. 5 shows the side profile of the probe housing placed on the temporal bone.

FIG. 5 shows the side profile of the probe housing placed on the temporal bone 27. A properly placed probe housing will have both the anterior and posterior ends of the probe stuck on the bone but the central portion free with couplant hydrogel 17 and hydrophilic polymer 18 trapped in the space between the acoustic window of the temporal bone and the transducer. To ensure that the desired probe-to-vessel angle is maintained the shape of the polypropylene base could appropriately be adapted. Additionally, the area around the couplant hydrogel 17 can be sealed to prevent leaks of the gel substance into the subcutaneous tissue by applying additional glue on the outside perimeter of the circular surface of the polypropylene base around the hydrophilic polymer 18.

Figure 6:
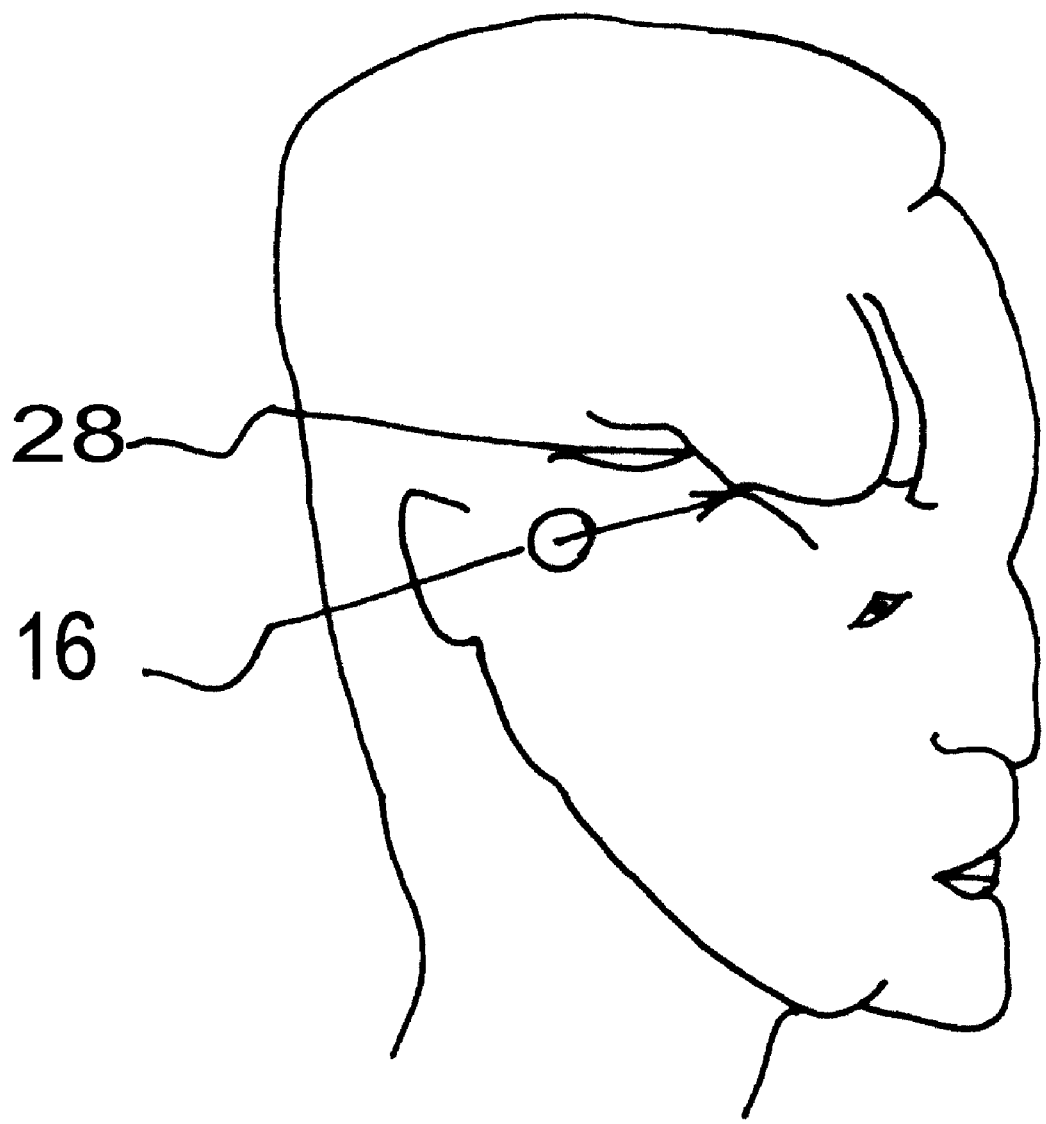
FIG. 6 shows the focusing of the transducer on basal cerebral arteries.

FIG. 6 shows the focusing of the transducer on basal cerebral arteries. The transducer 16 can be focused on any of the basal cerebral vessels. However, the preferred insonation is on the middle cerebral artery main stem 28 or at the carotid bifurcation (shown by arrow). The latter ensures monitoring of microembolic signal rate in a larger vascular territory.

Figure 7:
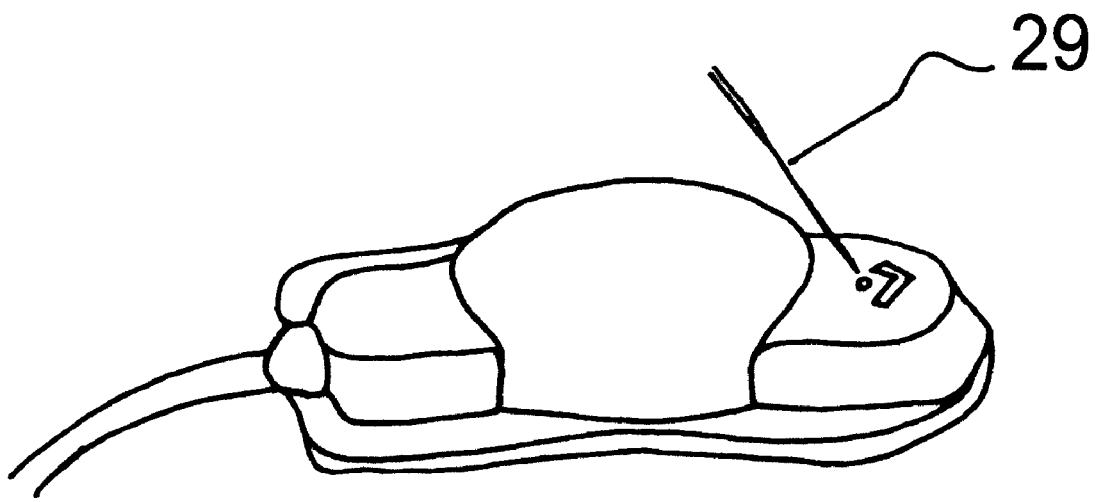
FIG. 7 shows the top-side view of the probe housing indicating the site of injection of the needle for percutaneous refills of ultrasonic gel substance.

FIG. 7 shows the top-side view of the probe housing indicating the site of needle introduction for percutaneous refills of ultrasonic gel substance. The radiopaque dot indicating the needle injection site 23 such as a 25-gauge needle 29 by way of example, allows for refill of the gel substance percutaneously under X-ray control. The radiopaque tantalum-impregnated arrowhead indicates the anterior end of the probe housing, and corresponds to the direction of the patient's face.

Figure 8:
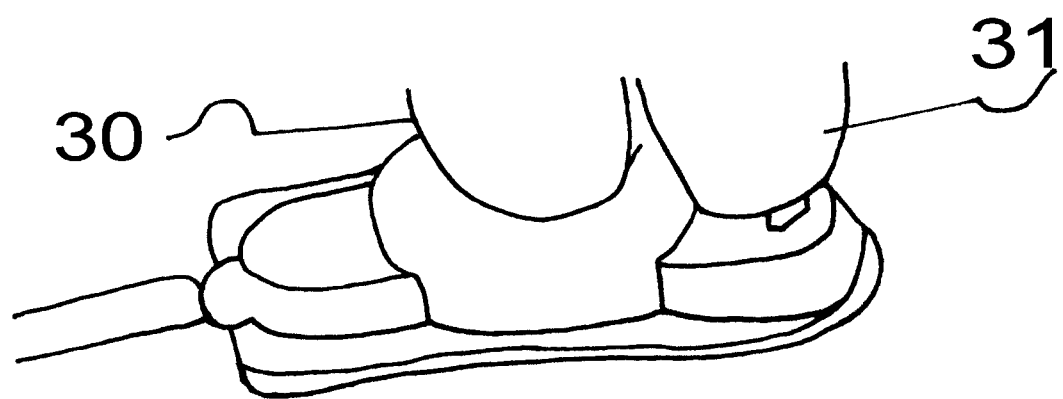
FIG. 8 shows the means to expunge the gel substance into to the space between the transducer and the temporal bone.

FIG. 8 shows the means to expunge the gel substance into the space between the transducer and the temporal bone. The middle 30 and index 31 fingers are used to press on the reservoir to expunge the gel substance into the space between the probe and the bone, until good contact of the gel sheet with the bone is achieved during implantation. This could be repeated percutaneously after implantation. Subsequently, it is not necessary to use fingers to expunge the gel substance. The system is designed such that the movement of the skin overlying the probe housing squeezes the dome of the probe housing against the temporal bone during talking and chewing or lying down on the side of the implant. This assures a regulated and continuing expunge of the gel substance via the outlets under the silicon membrane pump into the desired space between the probe and the bone. Doppler flow signal quality controls are used to determine when the hydrogel should be refilled.

Figure 9:
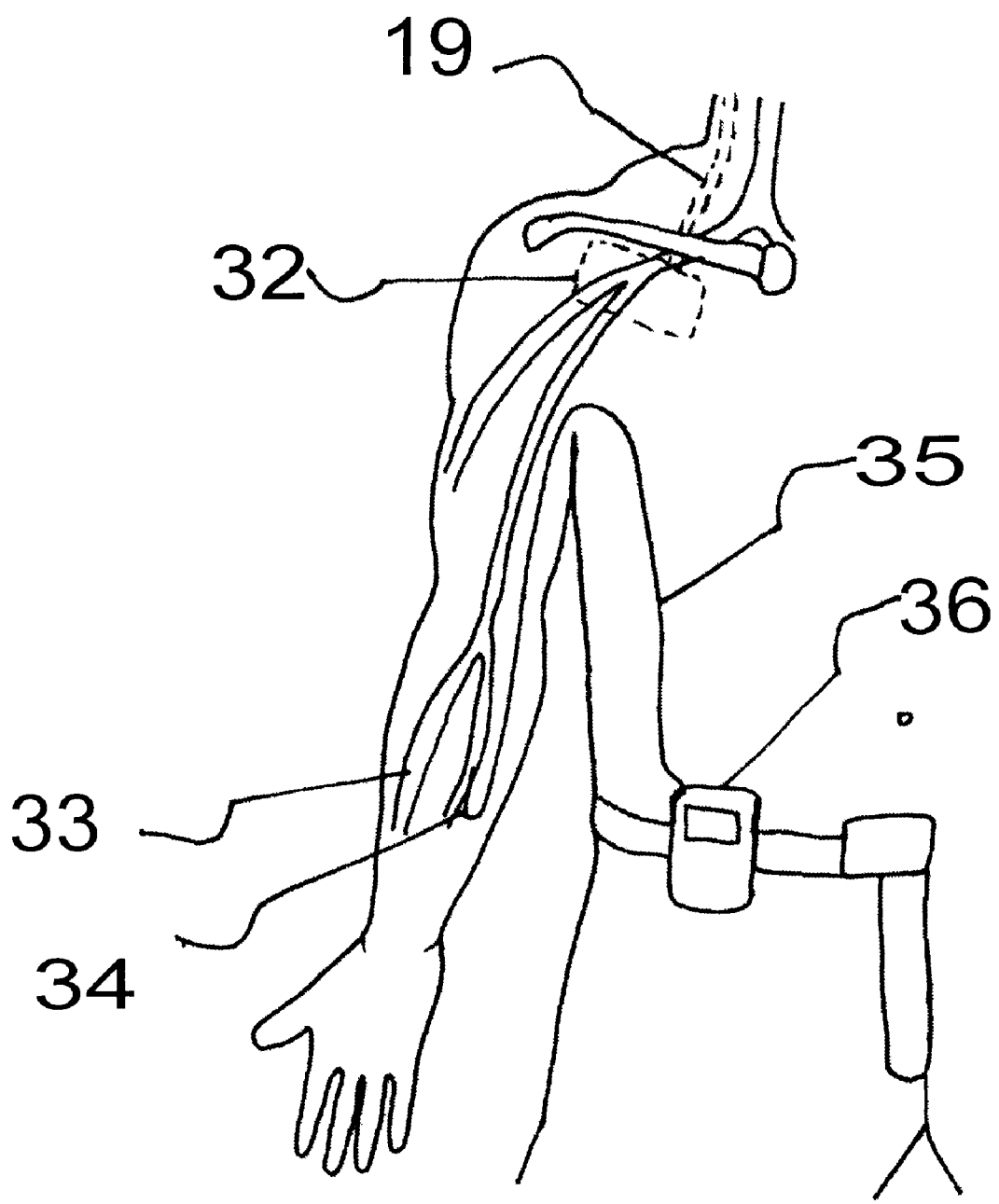
FIG. 9 shows the implantation of the transcranial Doppler ultrasound device inserted in a subcutaneous pocket below the clavicle.

FIG. 9 shows the implantation of the transcranial Doppler ultrasound device 32 inserted in a subcutaneous pocket below the clavicle. The components for assembly of such a transcranial Doppler ultrasound device and ultrasound transducers could be obtained from DWL, a company in Sipplingen, Germany. The transducer cable 19 is tunneled through the path from the temporal region to the space below the clavicle where the transcranial Doppler ultrasound device 32 is implanted. Making a small incision below and parallel to the clavicle to allow access to the subcutaneous pocket to insert the transcranial Doppler ultrasound device. When an internal infusion pump system is used, the catheter for delivery of the thrombolytic agent and/or neuroprotective agents is inserted into an in-vivo site for example the subclavian or cephalic vein. The pump could be connected directly to the transcranial Doppler ultrasound device. The implant site for the pump is chosen to permit percutaneous refill of the thrombolytic and/or neuroprotective agents. However, advances in genetic engineering may permit in-vivo production of the drug substances from cell lines, purification and storage in reservoir systems, with eventual dispensing of the drug by microinjection. Other modifications may include intra-peritoneal implantation with telemetric communication with the transcranial Doppler ultrasound device. However, in some cases where short duration use of a drug is of essence, external programmable infusion pump such as that used for insulin infusion for example Minimed 508 (Minimed Inc. Sylmar, Calif.) could be used with telemetric control by the transcranial Doppler ultrasound device. The infusion needle can be inserted into the veins of the arm such as the median antebrachial vein 33 using a catheter 34 and the infusion line 35 connected to the infusion pump 36 attached to a waist belt.

Figure 10:
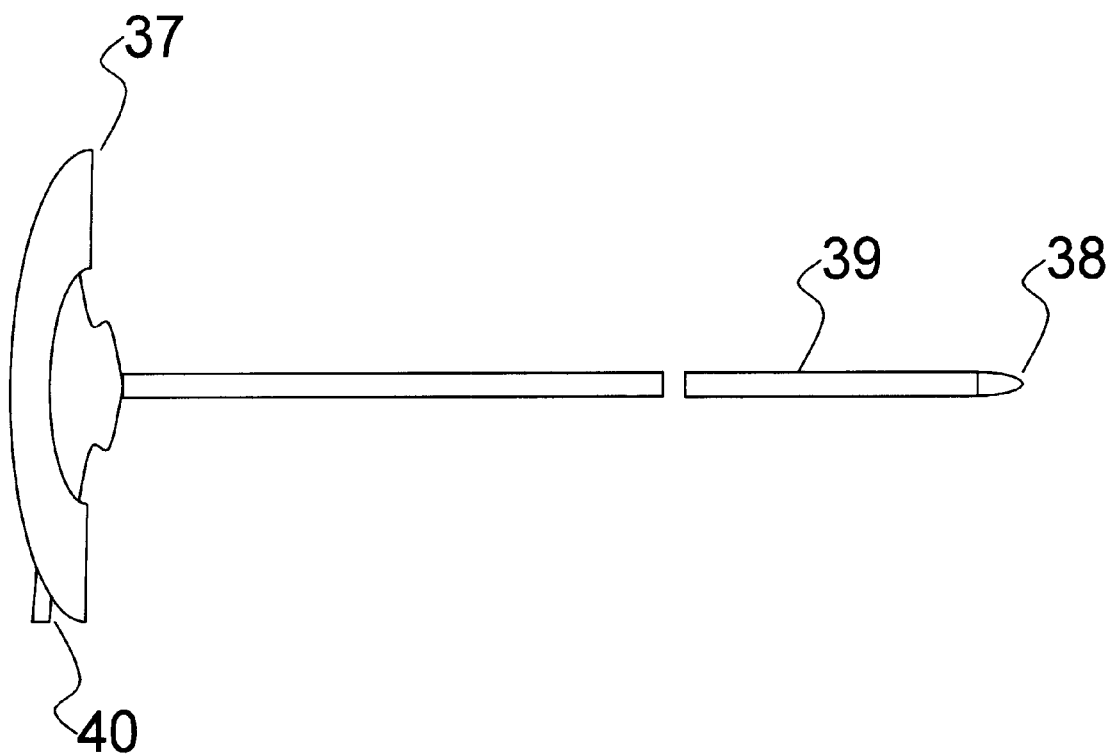
FIG. 10 shows the subcutaneous transducer cable passer.

FIG. 10 shows the subcutaneous transducer cable passer. The transducer cable passer is designed to pass distally through the subcutaneous space with the polypropylene handle 37 and nylon obturator 38 in place The tubular passer shaft 39 is malleable and may be hand formed by the surge on as required during the operative procedure. Tunneling of the subcutaneous space can be accomplished from either the top or bottom end as may be convenient for the surgeon. However, it is preferred that tunneling begins from behind the ear on the mastoid bone and along the stenocleidomastoid muscle to the clavicle. The passer will accept transducer cables of a definite outer diameter usually less than 3.0 mm by way of example. After placement of the passer, the obturator 38 is unlocked from the handle 37 and the handle removed from the passer shaft. The distal end connector (to the transcranial Doppler ultrasound device) of the transducer cable is then placed on the obturator end fitting 40 (that fits the transducer cable connector in a plug-to-socket arrangement). The obturator and transducer cable are then drawn through the passer shaft by pulling the distal obturator tip. The obturator is then removed from the transducer cable. The passer shaft can now be withdrawn caudally through the incision below the clavicle. The distal end of the transducer cable is now connected to the terminal on the transcranial Doppler ultrasound device.

Figure 11:
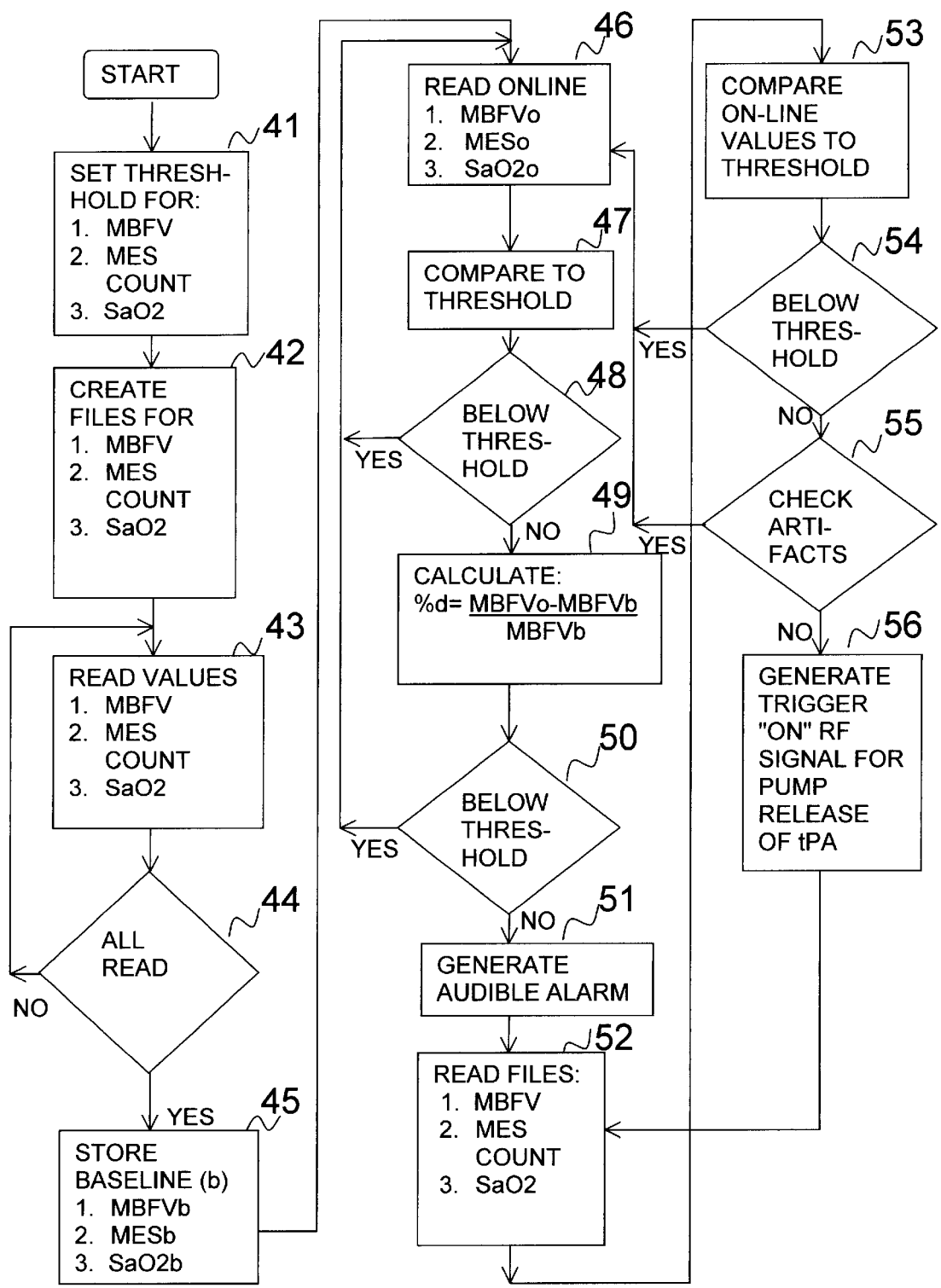
FIG. 11 shows the program flow chart of the invention.

FIG. 11 shows the program flow chart of the system of the invention. After initialization, the visualization of the operation of the transcranial Doppler device is done on the handheld computer, the telemetric connection between the handheld computer and the implanted transcranial Doppler device allows for telemetering of the Doppler signals for spectral display on the monitor of the handheld computer. The program mode selection could be done on the handheld computer. The implanted transcranial Doppler ultrasound device and the oximeter are all sensing devices for Doppler flow signals and oxygen saturation respectively; both signals are telemetered for analyses and display to the handheld computer. First, the threshold parameters 41 for mean blood flow velocity (MBFV) in the cerebral artery is set, the acceptable microembolic signal (MES) rate (count per unit time) is chosen and the normal oxygenation saturation level ($SaO_2$) range are selected. The program creates files 42 for storing the relevant data for these parameters. These parameters are read continually 43 and if not 44 all data are read, it proceeds to read all 43. If all are now read the program proceeds to store the baseline values 45 for the parameters monitored. It then reads the online values 46 and compares them to the set threshold 47, if the online values are below threshold 48 then it continues to read the online values 46. When above the set threshold, it calculates the precise percentage change in MBFV relative to baseline 49, if this is below the critical threshold 50 it continues with reading online values 46. However, if above the set threshold it generates an audible alarm 51, that cautions the patient (by a voice prompt, by way of example) to remain still for a few minutes, during which time it reads the files 52 and compares the online values to set threshold 53. If below threshold 54 it proceeds to read online parameters 46 in the usual manner. If above threshold it runs an artifact subroutine 55 to exclude such artifacts as motion related artifacts, sound interference, device malfunction and other artifacts that may arise. If the artifacts are confirmed, it proceeds with continuous monitoring of online parameters 46. If no artifacts were found, it generates the trigger "on" RF signal to cause the infusion to release a bolus of thrombolytic and/or neuroprotective agents such as rt-PA or Selfotel 56 into the vein of the patient. The event related files for the parameters are read 52 and transmitted to the handheld computer. From this point on, additional steps in the program could include activation of the global positioning system to provide the exact location of the patient to the emergency medical service team and the attending physician. Inclusion of a number of these options will appear obvious to anyone skilled in the art.

OTHER PUBLICATIONS

Aaslid R., et al., "Assessment of cerebral autoregulation dynamics from simultaneous arterial and venous transcranial Doppler recordings in humans," Stroke, vol. 22, pp. 1148–1154 (1991).

Alexandrov A. V., et al., "High rate of complete recanalization and dramatic clinical recovery during tPA infusion when continuously monitored with 2-MHz transcranial Doppler monitoring," Stroke, vol. 31, pp. 610–614 (2000).

Broderick J., et al., "The Greater Cincinnati/Northern Kentucky Stroke Study: preliminary first-ever and total incidence rates of stroke among blacks," Stroke, vol. 29, pp. 415–421 (1998).

Clark R. E., et al., "Microemboli during coronary artery bypass grafting genesis and effects on outcome," J Thorac Cardiovasc Surg, vol. 109, pp. 249–258 (1995). Consensus Committee of the Ninth International Cerebral Hemodynamic Symposium. "Basic identification criteria of Doppler microembolic signals," Stroke, vol. 26, p. 1123 (1995).

Cullinane M., et al., "Asymptomatic embolization in subjects with atrial fibrillation not taking anticoagulants: a prospective study," Stroke, vol. 29, pp. 1810–1815 (1998).

Davis S. M., et al., "Selfotel in acute Ischemic stroke. Possible neurotoxic effects of an NMDA antagonist," Stroke, vol. 30, pp. 347–345 (2000).

Diomedi M., et al., "Cerebral hemodynamic changes in sleep apnea syndrome and continuous positive airway pressure treatment," Neurology, vol. 51, pp. 1051–1056 (1998).

Frank O., "Die Grundform des arteriellen pulses," Z Biol, vol. 37, pp. 483–526 (1899).

Georgiadis D., et al., "Transcranial Doppler detection of microemboli in prosthetic heart valve patients: dependency upon valve type," Eur J Cardiothoracic Surg, vol. 10, pp. 253–258 (1996).
Grotta J. C., "Acute stroke therapy at the millennium: consummating the marriage between the laboratory and bedside: the Feinberg Lecture," Stroke, vol. 30, pp. 1722–1728 (1999).
Heiss W. D., et al., "Which targets are relevant for therapy of acute stroke" Stroke, vol. 30, pp. 1468–1489 (1999).
Kremkau F. W., "Diagnostic ultrasound: principles, instruments, and exercises," Third edition, W. B. Saunders Co., Philadelphia: (1989).
Lees K. R., "Cerestat and other NMDA antagonists in ischemic stroke," Neurology, vol. 49, pp. S66–S69 (1997).
Lauer C. G., et al., "Effect of ultrasound on tissue-type plasminogen activator thrombolysis," Circulation, vol. 86, 1257–1264 (1992).
Lewandowski C. A., et al., "Combined intravenous and intra-arterial rt-PA versus intra-arterial therapy of acute ischemic stroke: emergency management of stroke (EMS) bridging trial," Stroke, vol. 30, pp. 2598–2605 (1999).
National Institute of Neurological Disorders and Stroke rt-PA Stroke Study Group, "Tissue plasminogen activator for acute ischemic stroke," N Engl J Med, vol. 333, pp. 1581–1587 (1995).
Njemanze P. C., et al., "Fourier analysis of the cerebrovascular system," Stroke, vol. 22, pp. 721–726 (1991).
Njemanze P. C., "Handedness and carotid plaque lesion" Stroke, vol. 23, pp. 1679–1680 (1992).
Njemanze P. C., et al., "Cerebral blood flow velocity and EEG amplitude in generalized seizures: a case study," J Neuroimag, vol. 2, pp. 151–155 (1992).
Njemanze P. C., "Isoproterenol induced cerebral hypoperfusion in a heart transplant recipient," PACE vol. 16, pp. 491–495 (1992).
Njemanze P. C., "Critical limits of pressure flow relation in the human brain," Stroke, vol. 23, pp. 1743–1747 (1992).
Njemanze P. C., "Cerebrovascular dysautoregulation syndrome in a heart-lung transplant recipient," J Cardiovascular Tech, vol. 10, pp. 227–232 (1992),
Njemanze P. C., "Cerebral circulatory changes in a case of pacemaker syndrome," J Cardiovasc Technol, vol. 11, pp. 105–109 (1993).
Njemanze P. C., "Cerebral circulatory dysfunction and hemodynamic abnormalities in syncope during upright tilt test," Can J Cardiol, vol.9, pp. 238–242 (1993).
Njemanze P. C., "Cerebrovascular dysautoregulation syndrome complex—brain hypoperfusion precedes hypotension and cardiac asystole," Jpn Cir J, vol. 58, pp. 293–297 (1994).
Njemanze P. C., "Carotid stenosis determines impairment of ipsilateral dexterity in stroke," Stroke, vol. 31, pp. 293–297 (1994).
"Physicians' desk reference," 53rd edition, Medical Economics Company, Montvale, N.J.: pp. 1057–1061 (1999).
Simon R., and Shiraishi K., "N-methyl-D-aspartate antagonist reduces stroke size and regional glucose metabolism," Annals of Neurology, vol. 27, pp. 606–611 (1990).
Spencer M., "Transcranial Doppler monitoring and causes of stroke from carotid endarterectomy," Stroke, vol. 28, pp. 685–691 (1997).
Theron J. G., et al., "Carotid artery stenosis: treatment with protected balloon angioplasty and stent placement," Radiology, vol. 201, pp. 627–636 (1996).
Wagner W. R., and Johnson P. C., "Therapeutic techniques for reducing thrombosis after cardiovascular implants." In: Klizman B., (ed.) "Problems in General Surgery", J.B. Lippincott Co., Philadelphia, Pa.: chapter 11, pp. 241–246 (1994).
Wilhelm C. R., et al., "Measurement of hemostatic indexes in conjunction with transcranial Doppler Sonography in patients with ventricular assist devices," Stroke vol. 30, pp. 2554–2561 (1999).

What is claimed is:

1. A cerebral blood flow velocity monitoring system comprising:
   a transcranial Doppler ultrasound device adapted to be surgically implanted in the human body;
   a probe housing adapted to be surgically implanted on the temporal bone of the human head, said probe housing including the ultrasound transducer, and having a reservoir for refillable ultrasound gel;
   a surgically implantable transducer cable having a proximal end and a distal end oriented such that the proximal end is attached to the transducer and the distal end having a connector for the implanted transcranial Doppler ultrasound device; and
   an external handheld computer means for telemetering controlling signals to and receiving spectral signals from the implanted transcranial Doppler ultrasound device, the said handheld computer having a microcomputer, a monitor , input keyboard, a loud speaker, a communication means to the Internet and means of electrical power supply.

2. The system of claim 1 further including adhesive means on the probe housing base for fixation of the probe housing on the temporal bone and trapping the gel in place, so that the gel reservoir provides continuing coupling means between the ultrasound transducer and the temporal bone.

3. The system of claim 2 further wherein the implanted transcranial Doppler ultrasound device comprises a voltage generator/gate, receiver/gate, microprocessor, a radio-frequency transmitter/receiver and a battery power source.

4. The system of claim 3 further including oximeter means for measuring the oxygen saturation in blood, and communication means deriving signals responsive to the oxygen saturation and delivering said signals to the microprocessor of the transcranial Doppler ultrasound device.

5. The system of claim 4 further including a programming means for detection of microembolic signals, said programming means for regulation of infusion of medication for thrombolysis and neuroprotection.

6. The system of claim 5 further including an implantable drug infusion pump means for delivery of medication, said infusion pump operatively responsive to set threshold changes in cerebral blood flow velocity and rate of detection of microembolic signals.

7. The system of claim 6 further including a global positioning system means for determining the time and location of the event, said global positioning system operatively responsive to set threshold changes in cerebral blood flow velocity and rate of detection of microembolic signals.

8. The system of claim 7 further including an implanted pacemaker means for pacing the heart, said implanted pacemaker operatively responsive to set threshold changes in cerebral blood flow velocity.

9. The system of claim 7 further including a defibrillator means for ventricular defibrillation, said defibrillator operatively responsive to set threshold changes in cerebral blood flow velocity.

10. The system of claim 5 further including an external drug delivery system means for providing medication, said external drug delivery system operatively responsive to set threshold changes in cerebral blood flow velocity and rate of detection of microembolic signals.

11. The system of claim 4 further including a nasal continuous positive airway pressure device means for delivering breathing air, said nasal continuous positive airway pressure device is operatively responsive to set threshold changes in cerebral blood flow velocity and rate of detection of microembolic signals.

12. The system of claim 3 further including a programming means for detection of onset of seizures, said programming means for regulation of infusion of anti-epileptic medication.

13. The system of claim 6 further including a programming means for workload assessment.

14. A cerebral blood flow velocity monitoring system comprising:
- a transcranial Doppler ultrasound device adapted to be surgically implanted in the human body having a voltage generator/gate, a receiver/gate, a microprocessor, a radio-frequency transmitter, a connection terminal for the transducer cable and a battery power source;
- a surgically implantable silicon elastomer probe housing, said probe housing having a polypropylene base, said polypropylene base has an adhesive surface for fixation on the acoustic window of the temporal bone on the head, an ultrasound transducer with attached proximal end of the transducer cable, a reservoir made of silicon dome and having a valve;
- a surgically implantable transducer cable covered with kink resistant radiopaque silicon elastomer material, said transducer cable connected at the proximal end to the transducer and having at the distal end a connector; and
- an external handheld computer, said external handheld computer having a microcomputer, a monitor, input keyboard, a loudspeaker, a radio-frequency transmitter/receiver, a global positioning system, and a wire/wireless Internet communication.

15. The system of claim 14 further including an implantable drug infusion pump, said infusion pump for programmed delivery of medication and operatively responsive to set threshold of cerebral blood flow velocity and rate of detection of microembolic signals.

16. The system of claim 15 further wherein the sources of microembolic signals comprises vascular stent, vascular graft or prosthetic heart valves.

17. The system of claim 15 further wherein the source of microembolic signals comprises implanted ventricular assist devices.

18. A cerebral blood flow velocity monitoring system and method comprising:
- a transcranial Doppler ultrasound device adapted to be surgically implanted in the human body into a subcutaneous space by means of an incision below the clavicle and including a voltage generator/gate, a receiver/gate, a microprocessor, a radio-frequency transmitter and a battery power source;
- a surgically implantable silicon elastomer probe housing, said probe housing having a base made of polypropylene, said polypropylene base is adhesively fixated on the acoustic window of the temporal bone on the head and covered by skin above the zygomatic arc, and having an ultrasound transducer placed on the polypropylene base, said ultrasound transducer focused on a major cerebral vessel at a constant probe-to-vessel angle and coupled to the temporal bone with gel continually filled from a silicon dome reservoir, said reservoir externally refilled with gel under X-ray guidance via a radiopaque needle injection site, said gel expunged from the reservoir into the gel sheet placed in the space between the ultrasound transducer and the temporal bone;
- a surgically implantable transducer cable covered with kink resistant radiopaque silicon elastomer material, said transducer cable fixed at the proximal end to the ultrasound transducer and connected at the distal end to the transcranial Doppler ultrasound device by means of a connector, said transducer cable is tunneled subcutaneously from behind the ear on the mastoid bone and along the stenocleidomastoid muscle to the subcutaneous space below the clavicle by means of a transducer cable passer, said transducer cable passer comprising polypropylene handle, nylon obturator with end fitting and malleable tubular passer shaft; and
- an external handheld computer means for operatively controlling the internally implanted transcranial Doppler ultrasound device, said handheld computer having a microcomputer for processing data, a monitor means for displaying the spectral Doppler signals, input keyboard means for data entry and control of the functions of the system, a loudspeaker means for production of audio signals, a radio-frequency transmitter/receiver means for telemetering signals to and receiving signals from the internally implanted transcranial Doppler ultrasound device, a wire/wireless communication means to send and receive information on the Internet, a global positioning system means to locate the patient, and electrical power source means to provide electrical charge to the system;
- whereby the probe housing, the transducer cable and the transcranial Doppler ultrasound device are implanted using a specified operative procedure and methodology starting with an incision made on the skin covering the temporal bone, then the probe housing is placed on the temporal bone to allow insonation of the cerebral vessels using the ultrasound transducer to identify appropriate probe position, wherein the probe position is marked, and the bone surface prepared using an abrasive surgical instrument, then the adhesive polypropylene base of the probe housing is fixated to the bone, and the transducer cable is tunneled subcutaneously from behind the ear on the mastoid along the stenocleidomastoid muscle to below the clavicle using the transducer cable passer, the tunneling is accomplished by first placing the transducer cable passer in the subcutaneous space, then unlocking the obturator from the handle and removing the handle from the tubular shaft, and placing the distal end of the transducer cable with connector in the obturator end fitting so that the obturator and transducer cable are then drawn through the tubular shaft by pulling the distal obturator tip, the obturator is then removed from the transducer cable and the tubular shaft withdrawn caudally through the incision below the clavicle leaving the said transducer cable in place, the distal end connector of the transducer cable is then connected to the terminal at the transcranial Doppler ultrasound device, the said transcranial Doppler device is then implanted in the subcutaneous space below the clavicle, and the incision sites sutured.

19. The system of claim 18 further including an implanted refillable drug delivery system, said means for delivery of medication and operatively responsive to set threshold changes in cerebral blood flow velocity and rate of detection of microembolic signals.

20. The system of claim 19 further including an external drug delivery system, said means for delivery of medication and operatively responsive to set changes in cerebral blood flow velocity and rate of detection of microembolic signals.

* * * * *